(12) United States Patent
Ozeki et al.

(10) Patent No.: US 9,683,838 B2
(45) Date of Patent: Jun. 20, 2017

(54) ULTRASONIC MEASUREMENT METHOD AND ULTRASONIC MEASUREMENT APPARATUS

(71) Applicant: JFE STEEL CORPORATION, Tokyo (JP)

(72) Inventors: Takafumi Ozeki, Tokyo (JP); Yukinori Iizuka, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 376 days.

(21) Appl. No.: 14/414,652

(22) PCT Filed: Jul. 11, 2013

(86) PCT No.: PCT/JP2013/069043
§ 371 (c)(1),
(2) Date: Jan. 13, 2015

(87) PCT Pub. No.: WO2014/013940
PCT Pub. Date: Jan. 23, 2014

(65) Prior Publication Data
US 2015/0192412 A1      Jul. 9, 2015

(30) Foreign Application Priority Data

Jul. 17, 2012 (JP) .................................. 2012-159016
Jul. 17, 2012 (JP) .................................. 2012-159017

(51) Int. Cl.
*G01N 29/04* (2006.01)
*G01B 17/06* (2006.01)
(Continued)

(52) U.S. Cl.
CPC .......... *G01B 17/06* (2013.01); *G01N 29/043* (2013.01); *G01N 29/07* (2013.01); *G01N 29/28* (2013.01);
(Continued)

(58) Field of Classification Search
USPC ........................................ 73/598, 592, 622
See application file for complete search history.

(56) References Cited

U.S. PATENT DOCUMENTS 5,677,490 A * 10/1997 Gunther ............... G01N 29/043
73/620
6,640,632 B1 * 11/2003 Hatanaka ............. G01N 29/043
73/598

(Continued)

FOREIGN PATENT DOCUMENTS

CN        101300484 A    11/2008
CN        102095798 A     6/2011
(Continued)

OTHER PUBLICATIONS

Mar. 2, 2016 Search Report issued in European Patent Application No. 13820625.5.
(Continued)

*Primary Examiner* — Lam Nguyen
(74) *Attorney, Agent, or Firm* — Oliff PLC

(57) ABSTRACT

An ultrasonic measurement method includes: a measuring point setting step of setting an arbitrary measuring point near a weld portion inside of steel material and assuming a virtual reflecting surface that includes the measuring point and is parallel to a weld line direction; a focused beam setting step of transmitting ultrasonic waves of a shear wave mode and focusing onto the measuring point via a coupling medium at a predetermined incident angle with respect to the virtual reflecting surface; a detecting step of detecting reflected waves of the transmitted ultrasonic waves at a boundary between a base metal portion and the weld portion; and an evaluating step of evaluating a shape of the weld portion based on the reflected waves.

12 Claims, 17 Drawing Sheets

(51) Int. Cl.
*G01N 29/07* (2006.01)
*G01N 29/28* (2006.01)

(52) U.S. Cl.
CPC ........... *G01N 2291/0422* (2013.01); *G01N 2291/106* (2013.01); *G01N 2291/2634* (2013.01); *G01N 2291/2675* (2013.01)

(56) References Cited

U.S. PATENT DOCUMENTS

| | | | |
|---|---|---|---|
| 2009/0095087 A1* | 4/2009 | Yamano | G01N 29/043 73/622 |
| 2009/0151457 A1 | 6/2009 | Iizuka | |
| 2010/0107725 A1* | 5/2010 | Iizuka | G01N 29/11 73/1.82 |

FOREIGN PATENT DOCUMENTS

| | | |
|---|---|---|
| JP | A-2007-163470 | 6/2007 |
| JP | 2008-286640 A | 11/2008 |
| JP | A-2009-69077 | 4/2009 |
| JP | A-2009-233679 | 10/2009 |
| JP | A-2011-257384 | 12/2011 |

OTHER PUBLICATIONS

Oct. 15, 2013 International Search Report issued in International Patent Application No. PCT/JP2013/069043 (with translation).

Matsui et al; "Denpokan yosetsu hinshitsu no choonpa hihakai hyoka gijutsu no kaihatsu", The Japanese Society for Non Destructive Inspection Heisei 24 Nendo Shunki Koen Taikai Koen Gaiyoshu, May 22, 2012; pp. 9-12.

"Ultrasonic flaw detection test III" The Japanese Society for Non Destructive Inspection; 2001; pp. 24-25 (with partial translation).

"Ultrasonic flaw detection test II" The Japanese Society for Non Destructive Inspection; 2000; pp. 7-8 (with partial translation).

Apr. 18, 2016 Office Action issued in Chinese Patent Application No. 201380037425.3.

Hang, Shao-wen. "Software Design and Application of Ultrasonic Automatic Flaw Detection System of Welded Steel Pipes". Lossless Detection, Issue 6, vol. 30, Dec. 31, 2008, pp. 70-73.

Jul. 14, 2015 Office Action issued in Japanese Patent Applicaiton No. 2014-525805.

* cited by examiner

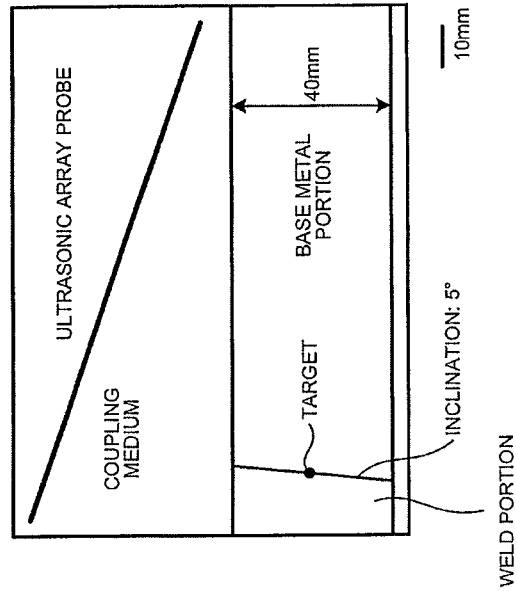

FIG.16

*SETTINGS OF PHYSICAL PROPERTIES

| | LONGITUDINAL WAVE VELOCITY (mm/s) | SHEAR WAVE VELOCITY (mm/s) | DENSITY (kg/mm³) |
|---|---|---|---|
| WATER | 1.48E+06 | 0.00E+00 | 1.00E-06 |
| STEEL | 5.92E+06 | 3.23E+06 | 7.80E-06 |
| WELD PORTION | 4.74E+06 | 2.58E+06 | 6.24E-06 |

| COMMON CONDITIONS | |
|---|---|
| TRANSMISSION FREQUENCY | 5MHz |
| NUMBER OF TRANSMISSION PULSES | MAXIMUM OF 2 |
| MESH WIDTH | 0.0296mm |
| STANDARD WATER DISTANCE | 30mm |
| VIBRATOR PITCH | 1.00mm |
| VIBRATOR WIDTH | 0.95mm |

| | INVENTION | CONVENTIONAL TECHNOLOGY |
|---|---|---|
| TRANSMITTING MODULE WIDTH | 19.9mm(20ch) | 5.9mm(6ch) |
| FOCUSING | FOCUSED | NON-FOCUSED |
| $\dfrac{V_T}{V_R} \cdot \dfrac{F}{D}$ | 2.2 | ∞ |
| INCIDENT ANGLE TO VIRTUAL REFLECTING SURFACE | 45° | 45° |
| RECEIVING MODULE WIDTH | 0.95mm(1ch) | 0.95mm(1ch) |

FIG. 22

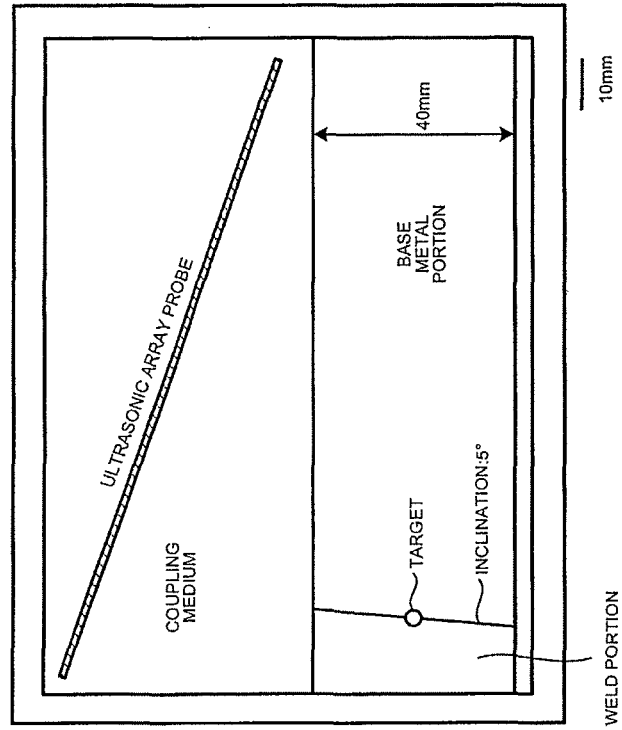

*SETTINGS OF PHYSICAL PROPERTIES

| | LONGITUDINAL WAVE VELOCITY (mm/s) | SHEAR WAVE VELOCITY (mm/s) | DENSITY (kg/mm³) |
|---|---|---|---|
| WATER | 1.48E+06 | 0.00E+00 | 1.00E-06 |
| STEEL | 5.92E+06 | 3.23E+06 | 7.80E-06 |
| WELD PORTION | 4.74E+06 | 2.58E+06 | 6.24E-06 |

| COMMON CONDITIONS | |
|---|---|
| TRANSMISSION FREQUENCY | 5MHz |
| NUMBER OF TRANSMISSION PULSES | MAXIMUM OF 2 |
| MESH WIDTH | 0.0296mm |
| STANDARD WATER DISTANCE | 30mm |
| VIBRATOR PITCH | 1.00mm |
| VIBRATOR WIDTH | 0.95mm |

| | VIRTUAL REFLECTING SURFACE P0 | VIRTUAL REFLECTING SURFACE P1 |
|---|---|---|
| TRANSMITTING MODULE WIDTH | 5.9mm(6ch) | 5.9mm(6ch) |
| FOCUSING | NON-FOCUSED | NON-FOCUSED |
| INCLINATION OF VIRTUAL REFLECTING SURFACE | 0° | 5° |
| INCIDENT ANGLE TO VIRTUAL REFLECTING SURFACE | 45° | 45° |
| RECEIVING MODULE WIDTH | 0.95mm(1ch) | 0.95mm(1ch) |

| SAMPLE No | SHEAR WAVE VELOCITY (10³m/s) | | | ESTIMATED REFLECTIVITY (ABSOLUTE VALUE) |
|---|---|---|---|---|
| | DISPLACE-MENT DIRECTION A | DISPLACE-MENT DIRECTION B | (AVERAGE) | |
| 1 | 3.21 | 3.24 | 3.23 | 0.2% |
| 2 | 3.23 | 3.23 | 3.23 | 0.0% |
| 3 | 3.21 | 3.22 | 3.23 | 0.2% |
| 4 | 3.23 | 3.22 | 3.23 | 0.2% |
| 5 | 3.22 | 3.23 | 3.23 | 0.0% |

ULTRASONIC MEASUREMENT METHOD AND ULTRASONIC MEASUREMENT APPARATUS

FIELD

The present invention relates to an ultrasonic measurement method and an ultrasonic measurement apparatus for evaluating the quality of a weld portion of steel material in a non-destructive manner by using ultrasonic waves.

BACKGROUND

It is known that a cross-sectional shape of a boundary of weld metal (weld portion) in a weld portion of steel material (hereinafter, a weld-boundary cross-sectional shape) influences the strength of the steel material. Patent Literature 1, for example, discloses that the weld-boundary cross-sectional shape of a weld portion of a steel pipe influences the toughness of the weld portion. Consequently, non-destructive evaluation technologies by imaging the weld-boundary cross-sectional shape have been developed in terms of quality control and quality assurance of the steel material. Patent Literature 2, for example, discloses an imaging technology by receiving reflected waves from a boundary between a base metal portion and a weld portion. Specifically, this technology makes an image by receiving reflected waves of ultrasonic waves transmitted at an angle toward the boundary between the base metal portion and the weld portion and identifying reflection points from the received reflected waves while moving a probe or switching vibrators (elements) of an array probe. Furthermore, Patent Literature 3 discloses a tandem measurement technology for detecting ultrasonic waves by separating a receiving device and a transmitting device of the ultrasonic waves.

In general, the orientation of crystal structure is aligned in a weld portion, and thus the weld portion has acoustic anisotropy. According to Patent Literature 1, for the steel material for which the acoustic anisotropy of weld portion is large such as austenitic stainless steel, the difference between acoustic impedance (=medium density×sound velocity) of base metal portion $Z_1$ and acoustic impedance of weld portion $Z_2$ is of a relatively large value. For example, when sound velocity of a base metal portion $V_1$ is 3200 m/s and sound velocity of a weld portion $V_2$ is 2500 m/s, because the medium density is a substantially constant value, the ratio of the acoustic impedance of the base metal portion $Z_1$ and the acoustic impedance of the weld portion $Z_2$ is 1 to 0.78.

Now, it is known that the reflectivity per unit area at an interface between different media depends on the acoustic impedance of both. According to Non-Patent Literature 1, the reflectivity (sound pressure) per unit area $r_{ab}$ at the interface when the ultrasonic waves are incident perpendicularly from the medium of acoustic impedance $Z_a$ to the medium of acoustic impedance $Z_b$ can be expressed as the following Expression 1.

$$r_{ab} = \frac{Z_b - Z_a}{Z_b + Z_a} \tag{1}$$

Thus, for the steel material in the foregoing example for which the acoustic anisotropy of the weld portion is large, the reflectivity per unit area $r_{12}$ at the interface when the ultrasonic waves are incident perpendicularly from the base metal portion of acoustic impedance $Z_1$ to the weld portion of acoustic impedance $Z_2$ is −0.12 according to Expression 1. The reflectivity in a negative value here represents that the phase of ultrasonic waves is inverted, and thus the reflectivity per unit area is 12%.

CITATION LIST

Patent Literature

Patent Literature 1: Japanese Patent Application Laid-open No. 2009-233679
Patent Literature 2: Japanese Patent Application Laid-open No. 2009-069077
Patent Literature 3: Japanese Patent Application Laid-open No. 2007-163470

Non-Patent Literature

Non-Patent Literature 1: Ultrasonic Flaw Detection Test III (2001), the Japanese Society for Non-Destructive Inspection

SUMMARY

Technical Problem

In general, the acoustic anisotropy of a weld portion of carbon steel is smaller than that of a weld portion of austenitic stainless steel. FIG. 25 is a diagram illustrating a shear wave velocity measured at a weld portion of carbon steel welded by conventional submerged arc welding and the reflectivity calculated based on the measured sound velocity. As illustrated in FIG. 25, in the weld portion of carbon steel, there is little difference in the shear wave velocity between the displacement direction A parallel to a weld line direction and the displacement direction B perpendicular to the weld line direction.

For this carbon steel, the reflectivity per unit area of ultrasonic waves that are incident perpendicularly from the base metal portion to the weld portion at the interface was calculated by Expression 1. When calculating the reflectivity per unit area, the medium density of the base metal portion and that of the weld portion were assumed to be equal. The shear wave velocity of the base metal portion was defined as the average value of the shear wave velocity in the displacement direction A parallel to the weld line direction in the weld portion and the shear wave velocity in the displacement direction B perpendicular to the weld line direction, and the shear wave velocity of the weld portion was defined as the shear wave velocity in the displacement direction B perpendicular to the weld line direction in the weld portion.

The calculated reflectivity per unit area was 0.0 to 0.2%, as illustrated in FIG. 25, and is a value as small as ⅟₆₀th of the reflectivity per unit area (12%) at the interface between the base metal portion and the weld portion of the foregoing austenitic stainless steel. Consequently, in the carbon steel for which the acoustic anisotropy of weld portion is small, it suggests that it is difficult to detect the reflected waves of the ultrasonic waves that are incident perpendicularly from the base metal portion to the weld portion at the boundary.

Next, discussed are reflected waves of the ultrasonic waves that are incident at an incident angle a from the base metal portion to the weld portion. According to Non-Patent Literature 1, when ultrasonic waves are incident at an incident angle α on a belt-like reflector of a width $2a$ having 100% reflectivity per unit area, the overall reflectivity in the direction of reflection angle β (=Total reflected sound pressure/Total incident sound pressure) r'(α,β) can be expressed as the following Expression 2 by using the number of waves k.

$$r'(\alpha, \beta) = \frac{\sin(ka(\sin\beta - \sin\alpha))}{ka(\sin\beta - \sin\alpha)} \quad (2)$$

Note that the number of waves k can be expressed as the following Expression 3 by using wavelength λ. Furthermore, among the wavelength λ, the frequency f, and the sound velocity V, the relation in the following Expression 4 holds true.

$$k = \frac{2\pi}{\lambda} \quad (3)$$

$$V = f\lambda \quad (4)$$

Now, discussed is the reflection at the boundary between the base metal portion and the weld portion. The interface between the base metal portion and the weld portion as a reflector is assumed to be fully extended in the thickness direction of the steel material. Furthermore, the item a (=Width of reflector/2) in Expression 2 is defined as 10 mm. In general, for the transversal wave oblique flaw detection of steel material, the ultrasonic waves of f=5 MHz and V=3200 m/s, that is, λ=0.64 mm are used. At this time, the overall reflectivity r'(45°, −45°) when the ultrasonic waves that are incident at an incident angle of 45° are reflected at a reflection angle of −45° (reflected to the incident direction) is 0.0003. Note that this value is a value calculated for the reflector having the reflectivity per unit area of 100%. More specifically, when the acoustic anisotropy of weld portion is small as is the carbon steel in particular, the above-described overall reflectivity is of an extremely small value, and thus it can tell that, as described in Patent Literature 2, it is difficult to identify the boundary between the base metal portion and the weld portion by receiving the reflected waves that are reflected in the incident direction.

Now, discussed is the detection of reflected waves of the ultrasonic waves that are incident at the incident angle α from the base metal portion to the weld portion of carbon steel, for which the acoustic anisotropy of weld portion is small, by tandem measurement. According to the tandem measurement described in Patent Literature 3, the transmitting device and the receiving device only need to be selected appropriately such that the incident angle α and the reflection angle β are to be equal. In that case, the overall reflectivity r'(α, α) is 1 regardless of k and a, and strong reflected waves can be obtained.

In the tandem measurement, a virtual reflecting surface is assumed and the transmitting device and the receiving device of the ultrasonic waves are selected such that the incident angle α and the reflection angle β are to be the equal value α with respect to the virtual reflecting surface. At that time, if the orientation of the virtual reflecting surface is deviated from the orientation of the actual reflecting surface, the incident angle α and the reflection angle β with respect to the virtual reflecting surface are deviated from the incident angle and the reflection angle with respect to the actual reflecting surface. By defining this deviation angle as θ, the overall reflectivity r'(α+θ, α−θ) of the actual reflecting surface can be obtained from the foregoing Expression 2.

FIG. 26 is a diagram illustrating the reflectivity when a=10 mm, f=5 MHz, V=3200 m/s, and α=45° in Expression 2. As illustrated in FIG. 26, the overall reflectivity r'(45°+θ, 45°−θ) of the actual reflecting surface to be 50% or greater is when the deviation angle θ is in the range of −0.8° to 0.8°. Consequently, even in the tandem measurement, the detection of the reflected waves is difficult if the deviation angle θ between the actual reflecting surface and the virtual reflecting surface is 1° or greater.

As in the foregoing, according to the conventional technologies, for the carbon steel for which the acoustic anisotropy of weld portion is small, even by the tandem measurement, it has been difficult to detect the reflected waves of ultrasonic waves reflected at the boundary between the base metal portion and the weld portion.

In view of the foregoing, it is an object of the present invention to provide an ultrasonic measurement method and an ultrasonic measurement apparatus that can easily detect the ultrasonic waves reflected at the boundary between the base metal portion and the weld portion of steel material.

Solution to Problem

To solve the above-described problems and achieve the object, an ultrasonic measurement method according to the present invention includes: a measuring point setting step of setting an arbitrary measuring point near a weld portion inside of steel material and assuming a virtual reflecting surface that includes the measuring point and is parallel to a weld line direction; a focused beam setting step of transmitting ultrasonic waves of a shear wave mode satisfying Expression 5 and focusing onto the measuring point via a coupling medium at a predetermined incident angle with respect to the virtual reflecting surface; a detecting step of detecting reflected waves of the transmitted ultrasonic waves at a boundary between a base metal portion and the weld portion; and an evaluating step of evaluating a shape of the weld portion based on the reflected waves:

$$\frac{V_T}{V_R} \cdot \frac{F}{D} \leq \frac{0.30}{\sin\theta_{Hlim}} \quad (5)$$

where $V_T$ (mm/s) is sound velocity of the coupling medium, $V_R$ (mm/s) is sound velocity of shear waves at the base metal portion of the steel material as a test subject, D (mm) is a transmitting unit width in a direction orthogonal to the weld line direction, F (mm) is a focal length in coupling medium conversion, and $\theta_{Hlim}$ (degrees) is a deviation angle upper limit between the assumed reflecting surface and an actual reflecting surface.

Moreover, in the above-described ultrasonic measurement method according to the present invention, a plurality of virtual reflecting surfaces of different angles are assumed for each measuring point set at the measuring point setting step.

Moreover, in the above-described ultrasonic measurement method according to the present invention, the virtual reflecting surfaces for which areas in a normal direction are continuous are assumed such that transmission and reception efficiency of at least one of the virtual reflecting surfaces is 0.5 or higher while the transmission and reception efficiency is 1 when the virtual reflecting surface coincides with an actual reflecting surface.

Moreover, in the above-described ultrasonic measurement method according to the present invention, the deviation angle upper limit $\theta_{Hlim}$ is 2°.

Moreover, in the above-described ultrasonic measurement method according to the present invention, the base metal portion of the steel material satisfies Expression 6 with respect to sound velocity $V_{max}$ in a mode in which the sound velocity is maximized and sound velocity $V_{min}$ in a mode in which the sound velocity is minimized:

$$2.5 \times 10^{-3} \leq \frac{V_{max} - V_{min}}{V_{max} + 3V_{min}}. \quad (6)$$

Moreover, in the above-described ultrasonic measurement method according to the present invention, the incident angle is an angle formed between a transmission direction of the ultrasonic waves and a normal direction of the virtual reflecting surface at the measuring point and is 0° or greater and 10° or smaller or is 35° or greater and 55° or smaller.

Moreover, in the above-described ultrasonic measurement method according to the present invention, transmission and reception of the ultrasonic waves are performed while changing the measuring point by using an array probe for the transmission and reception of the ultrasonic waves and by switching electronic beam control of the array probe.

Moreover, an ultrasonic measurement apparatus according to the present invention includes: a measuring-point setting unit that sets an arbitrary measuring point near a weld portion inside of steel material and assumes a virtual reflecting surface that includes the measuring point and is parallel to a weld line direction; a focused-beam setting unit that transmits ultrasonic waves of a shear wave mode satisfying Expression 7 and focusing onto the measuring point via a coupling medium at a predetermined incident angle with respect to the virtual reflecting surface; a detector that detects reflected waves of the transmitted ultrasonic waves at a boundary between a base metal portion and the weld portion; and an evaluating unit that evaluates a shape of the weld portion based on the reflected waves:

$$\frac{V_T}{V_R} \cdot \frac{F}{D} \leq \frac{0.30}{\sin\theta_{Hlim}} \quad (7)$$

where $V_T$ (mm/s) is sound velocity of the coupling medium, $V_R$ (mm/s) is sound velocity of shear waves at the base metal portion of the steel material as a test subject, D (mm) is a transmitting unit width in a direction orthogonal to the weld line direction, F (mm) is a focal length in coupling medium conversion, and $\theta_{Hlim}$ (degrees) is a deviation angle upper limit between the assumed reflecting surface and an actual reflecting surface.

To solve the above-described problems and achieve the object, an ultrasonic measurement method according to the present invention includes, measuring point setting to set an arbitrary measuring point near a weld portion inside of steel material and to assume a plurality of reflecting surfaces of different angles which include the measuring point and are parallel to a weld line direction, ultrasonic beam setting to transmit ultrasonic waves of a shear wave mode to the measuring point via a coupling medium at a predetermined incident angle with respect to each of the reflecting surfaces, detecting reflected waves of the transmitted ultrasonic waves at a boundary between a base metal portion and the weld portion, and evaluating the shape of the weld portion based on the reflected waves.

Furthermore, an ultrasonic measurement apparatus according to the present invention includes a measuring-point setting module that sets an arbitrary measuring point near a weld portion inside of steel material and assumes a plurality of reflecting surfaces of different angles which include the measuring point and are parallel to a weld line direction, an ultrasonic-beam setting unit that transmits ultrasonic waves of a shear wave mode to the measuring point via a coupling medium at a predetermined incident angle with respect to each of the reflecting surfaces, a detector that detects reflected waves of the transmitted ultrasonic waves at a boundary between a base metal portion and the weld portion, and an evaluation unit that evaluates the shape of the weld portion based on the reflected waves.

Advantageous Effects of Invention

In accordance with the present invention, the ultrasonic waves reflected at the boundary between the base metal portion and the weld portion of steel material can be detected easily.

BRIEF DESCRIPTION OF DRAWINGS

FIG. 16 is a diagram illustrating the setting conditions in a first example.

FIG. 22 is a diagram illustrating the setting conditions in a second example.

DESCRIPTION OF EMBODIMENTS

With reference to the accompanying drawings, the following describes exemplary embodiments of the present invention. Note that the invention is not intended to be limited by the embodiments. Furthermore, in the description of the drawings, the same portions are denoted by the same reference signs.

First Embodiment
Acoustic Anisotropy of Base Metal Portion of Steel Material

First, described is carbon steel as a test subject in a first embodiment. Conventionally, because the acoustic anisotropy of a weld portion of carbon steel is small, it has been difficult to detect reflected waves at the boundary between a base metal portion and the weld portion. However, in the case that the base metal portion has the acoustic anisotropy even though being the carbon steel, the reflected waves at the boundary between the base metal portion and the weld portion are detectable. Consequently, in the first embodiment, with the carbon steel, for which the base metal portion has the acoustic anisotropy, as a test subject, the reflected waves of ultrasonic waves at an interface between the base metal portion and the weld portion are measured. The degree of acoustic anisotropy of the base metal portion necessary in the first embodiment will be described later.

Configuration of Apparatus

Figure 1:
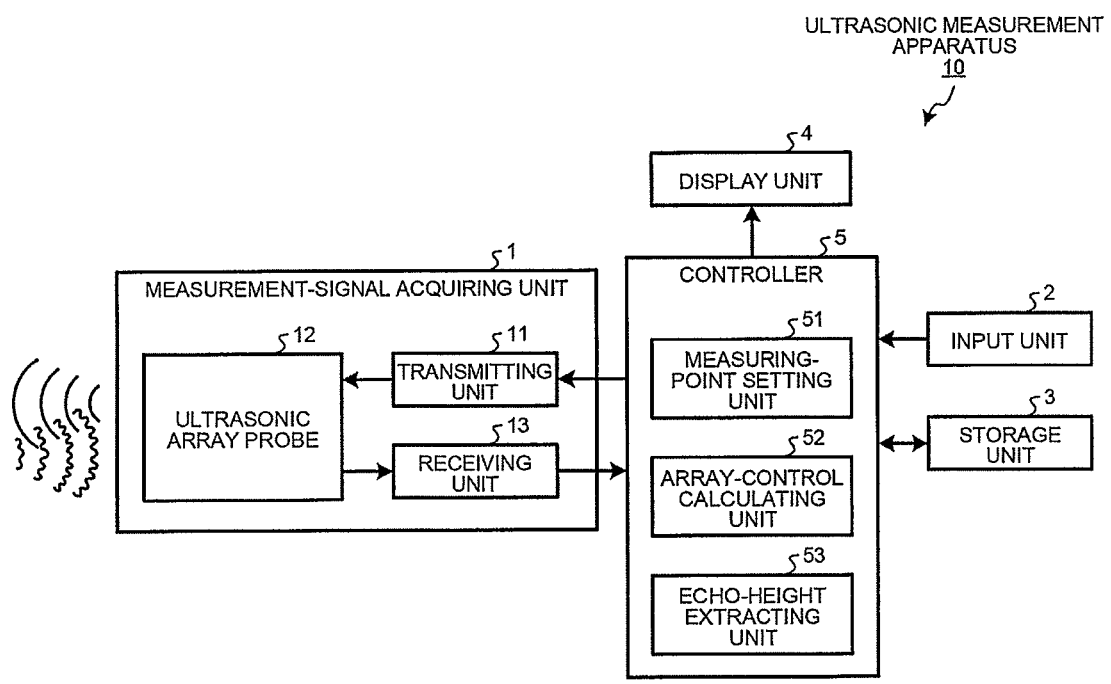
FIG. 1 is a block diagram schematically illustrating the configuration of an ultrasonic measurement apparatus according to an embodiment of the invention.

Next, described is the configuration of an ultrasonic measurement apparatus that is one embodiment of the invention. FIG. 1 is a block diagram schematically illustrating the configuration of the ultrasonic measurement apparatus in the first embodiment. As illustrated in FIG. 1, this ultrasonic measurement apparatus 10 includes a measurement-signal acquiring unit 1 that transmits ultrasonic waves to a test subject and receives an ultrasonic signal (measurement signal) attributable to the transmitted ultrasonic waves, an input unit 2 to which a variety of information is entered, a storage unit 3 that stores therein measurement data of the test subject and others, a display unit 4 that displays measurement results of the test subject and others, and a controller 5 that controls various constituent units of the ultrasonic measurement apparatus 10.

The measurement-signal acquiring unit 1 performs tandem measurement in which an ultrasonic signal of an electrical signal transmitted from a transmitting unit 11 is transmitted from an ultrasonic array probe 12 to the outside as ultrasonic waves, and the ultrasonic waves received by the ultrasonic array probe 12 are output to a receiving unit 13 as an ultrasonic signal of an electrical signal. The ultrasonic array probe 12 is implemented by using a piezoelectric vibrator or the like, transmits ultrasonic waves to the outside by the application of a pulse signal from the transmitting unit 11, receives the ultrasonic waves from the outside, and converts them to an electrical signal. The transmitting unit 11 outputs ultrasonic waves from the ultrasonic array probe 12 to the outside by applying a pulse signal, the frequency of which is at or near the resonant frequency of the ultrasonic array probe 12, to the ultrasonic array probe 12.

The input unit 2 is implemented by using an input device such as a power switch and input keys. Furthermore, the input unit 2 inputs, in response to input operation by an operator, various types of command information to the controller 5. For example, the input unit 2 inputs to the controller 5 the command information such as command information to start or stop the measuring of a test subject and command information instructing the display or storage of measurement data of the test subject.

The storage unit 3 is implemented by using a storage medium such as a hard disk, and stores therein a variety of information such as the measurement data of a test subject instructed by the controller 5.

The display unit 4 is implemented by using a display device such as a liquid crystal display, and displays a variety of information instructed to be displayed by the controller 5. Specifically, the display unit 4 displays the measurement data of a test subject by ultrasonic measurement.

The controller 5 includes a measuring-point setting unit 51, an array-control calculating unit 52, and an echo-height extracting unit 53, and controls the foregoing various constituent units of the ultrasonic measurement apparatus 10. Specifically, the controller 5 is implemented by using a memory that stores therein processing programs and others, a CPU that executes the processing programs, and others. The controller 5 controls, for example, the timing of respective operation of the measurement-signal acquiring unit 1, the storage unit 3, and the display unit 4 in the foregoing.

Ultrasonic Measurement Processing

Figure 2:
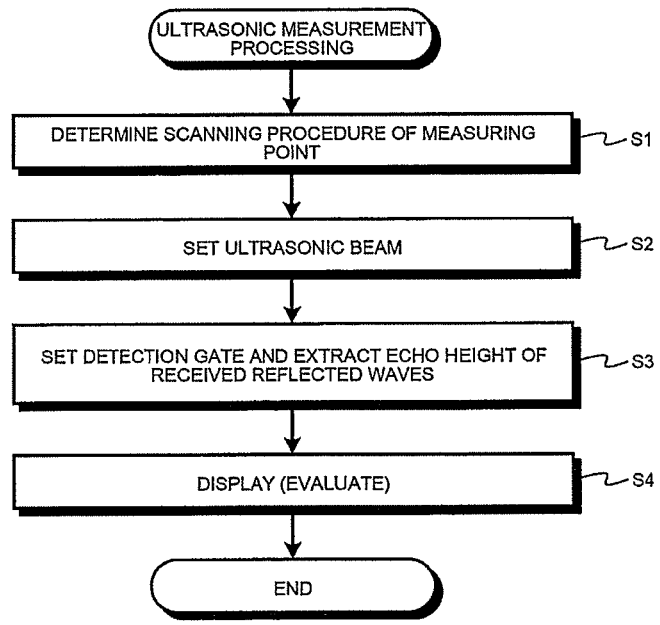
FIG. 2 is a flowchart illustrating a procedure of ultrasonic measurement processing performed by the ultrasonic measurement apparatus.

Now, with reference to the flowchart illustrated in FIG. 2, described is a procedure of ultrasonic measurement processing performed by the ultrasonic measurement apparatus 10. The flowchart in FIG. 2 is started at the timing of receiving an input of an ultrasonic measurement command for a test subject by the operator, for example, and the ultrasonic measurement processing advances to the process at Step S1.

In the process at Step S1, the measuring-point setting unit 51 determines a scanning procedure of measuring point. This completes the process at Step S1, and the ultrasonic measurement processing advances to the process at Step S2.

Figure 3:
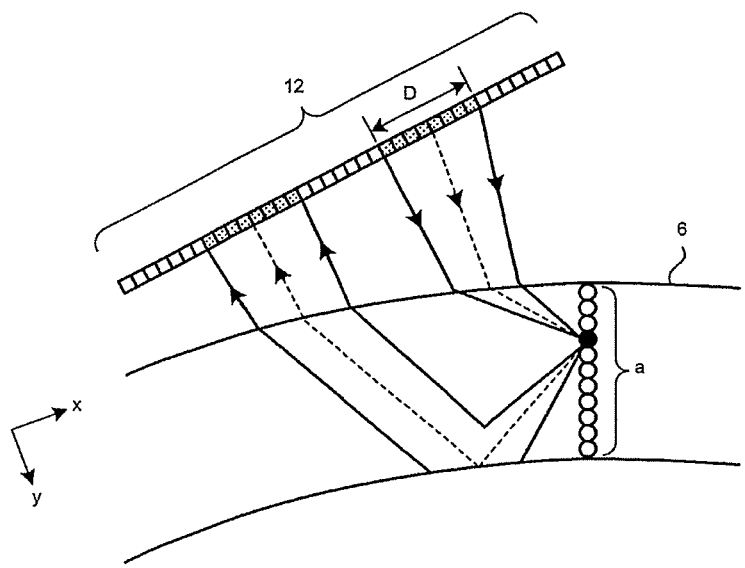
FIG. 3 is a schematic diagram illustrating a plurality of measuring points as targets of an ultrasonic array probe.
Figure 4:
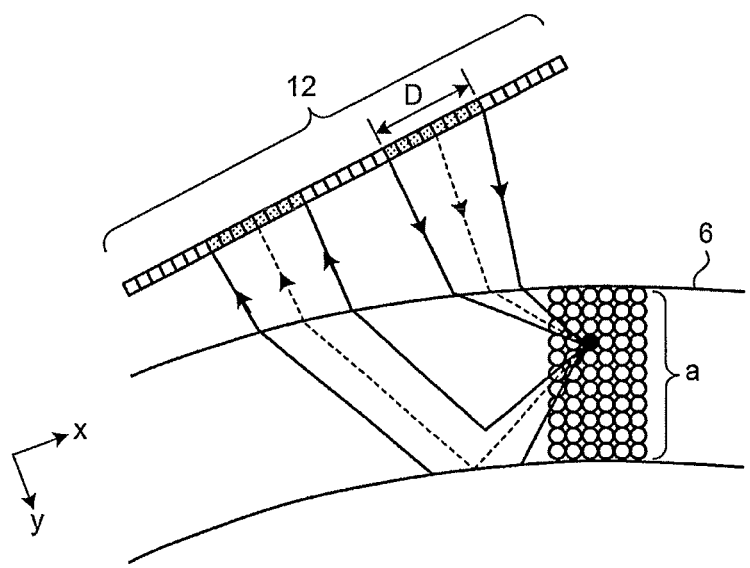
FIG. 4 is a schematic diagram illustrating a plurality of measuring points as targets of the ultrasonic array probe.
Figure 5:
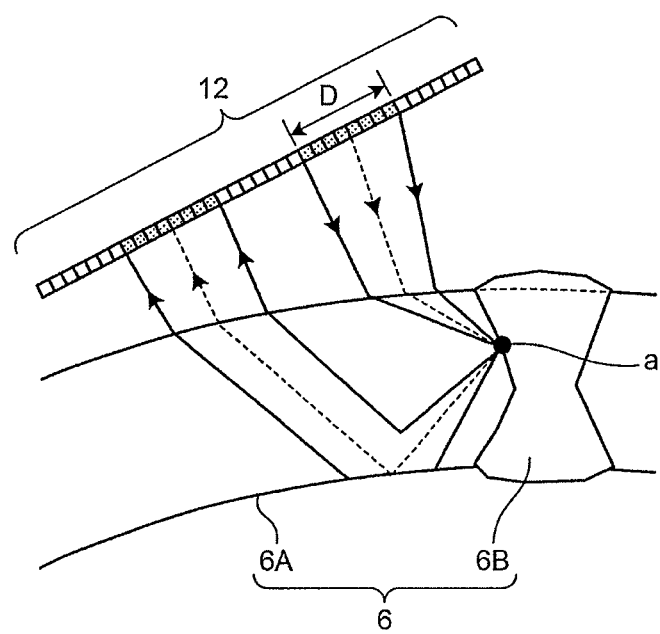
FIG. 5 is a schematic diagram illustrating a measuring point of steel material as a target of the ultrasonic array probe.

Now, with reference to FIGS. 3 and 4, described is the scanning procedure of measuring point performed by the measuring-point setting unit 51. FIGS. 3 and 4 are schematic diagrams illustrating a plurality of measuring points in a tubular test subject as targets of the ultrasonic array probe 12. Each of the circle marks in FIGS. 3 and 4 represents a measuring point a. FIG. 5 is a schematic diagram illustrating a measuring point in steel material as a target of the ultrasonic array probe 12 in the first embodiment.

As illustrated in FIG. 3, the ultrasonic array probe 12 transmits ultrasonic waves (shear wave mode) to a plurality of measuring points a distributed in a sheet thickness (wall thickness) direction y of a tubular test subject 6 as targets, and while scanning in the sheet thickness direction y, the ultrasonic array probe 12 measures reflected waves. Subsequently, by combining with a mechanical scanning in a circumferential direction x, the ultrasonic array probe 12 can acquire a two-dimensional image of the sheet thickness direction y and the circumferential direction x representing measurement results. Note that the ultrasonic array probe 12 is kept in an arbitrary position with respect to the test subject 6 at the time of mechanical scanning of the ultrasonic array probe 12 in the circumferential direction x.

Alternatively, as illustrated in FIG. 4, with a plurality of measuring points a two-dimensionally distributed in the sheet thickness (wall thickness) direction y and the circumferential direction x of the tubular test subject 6 as targets, the ultrasonic array probe 12 measures the reflected waves while scanning in the sheet thickness direction y and the circumferential direction x. In this case, the ultrasonic array probe 12 can acquire a two-dimensional image representing the measurement results without performing the mechanical scanning.

FIG. 5 is a schematic diagram illustrating a measuring point of steel material as a target of the ultrasonic array probe 12 in the first embodiment. As illustrated in FIG. 5, in the first embodiment, the measuring point a located inside a base metal portion 6A of the test subject 6 near a weld portion 6B is defined as a target.

In the process at Step S2, the array-control calculating unit 52 sets an ultrasonic beam of the ultrasonic array probe 12. The array-control calculating unit 52 first selects a group of transmitting devices and a group of receiving devices of the ultrasonic array probe 12. More specifically, the array-control calculating unit 52 calculates an incident direction and a reflection direction with respect to a virtual reflecting surface (virtual reflecting surface assumed such that the incident angle and the reflection angle are of an equal value α), and selects the center of the group of transmitting devices and the center of the group of receiving devices so as to satisfy the incident direction and the reflection direction. At that time, the array-control calculating unit 52 selects the group of transmitting devices so as to satisfy a transmitting unit width D calculated in setting of a focused beam which will be described later.

Next, the array-control calculating unit 52 calculates propagation paths of the respective selected devices, and based on the calculated propagation paths, calculates the propagation time of the respective devices. The array-control calculating unit 52 then sets the delay time of the respective devices in transmission (or in reception) based on the calculated propagation time such that the ultrasonic beam focuses onto the respective measuring points. This completes the process at Step S2, and the ultrasonic measurement processing advances to the process at Step S3.

In the process at Step S3, the echo-height extracting unit 53 performs the setting of detection gate and detects the intensity of the received reflected waves. More specifically, the echo-height extracting unit 53 sets the detection gate based on the propagation time calculated by the array-control calculating unit 52, and extracts the echo height of the reflected waves received during that period.

Figure 6:
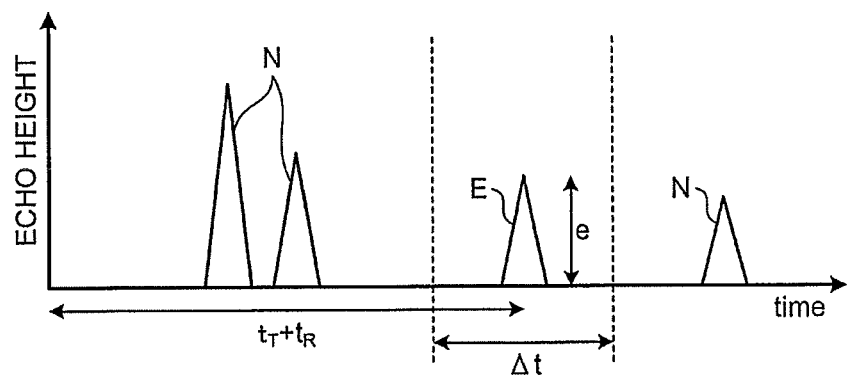
FIG. 6 is a chart for explaining the method of setting a detection gate.

FIG. 6 is a chart for explaining the method of setting a detection gate. As illustrated in FIG. 6, the echo-height extracting unit 53 receives the reflected waves (echo) E by opening a detection gate At only when the reflected waves that are transmitted from the transmitting device and reflected at the measuring point reach the receiving device, that is, an arbitrary time zone in the vicinity of the transmission-side propagation time (propagation time from the transmitting device to the measuring point) $t_T$ plus the receiving-side propagation time (propagation time from the measuring point to the receiving device) $t_R$, and extracts the echo height e of the reflected waves E. This eliminates the influence of spurious echoes N and enables only the reflected waves E at the measuring point to be detected. This completes the process at Step S3, and the ultrasonic measurement processing advances to the process at Step S4.

Note that if there is no virtual reflecting surface, the setting of detection gate is unnecessary. Furthermore, because the transmission-side (from the transmitting device to the measuring point) propagation time is different from the receiving-side (from the measuring point to the receiving device) propagation time depending on the measuring point, the detection gate is changed appropriately corresponding to the measuring point.

Figure 7:
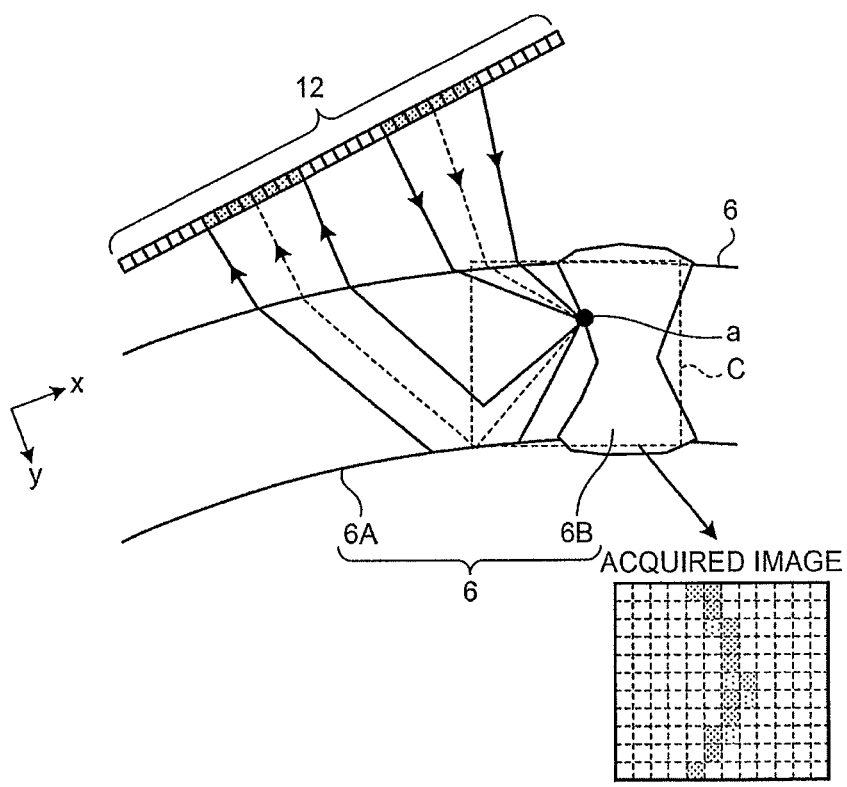
FIG. 7 is a diagram for explaining the output of measurement results to a display unit.

In the process at Step S4, the controller 5 outputs measurement results to the display unit 4, thereby the weld-boundary cross-sectional shape is evaluated. FIG. 7 is a diagram for explaining the output of measurement results to the display unit 4. More specifically, as illustrated in FIG. 7, the controller 5 displays an image by setting, for each of the measuring points a in an evaluation target area C, the luminance corresponding to the echo height of measurement result at the pixel position identified by the position of the ultrasonic array probe 12 separately detected and the position of the measuring point a determined by the measuring-point setting unit 51. Thus, the image representing the weld-boundary cross-sectional shape is displayed on the display unit 4. This completes the process at Step S4, and ends a series of ultrasonic measurement processing.

Requirements for Acoustic Anisotropy of Base Metal Portion of Steel Material

In the carbon steel as the test subject in the first embodiment, described is the degree of acoustic anisotropy of base metal portion necessary at the time of measuring the reflected waves of ultrasonic waves by tandem measurement. In general, it is known that the size of flaw detectable by the tandem measurement with the beam diameter of approximately 0.7 millimeters is from several tens of micrometers to 100 micrometers (see Patent Literature 3).

Figure 8:
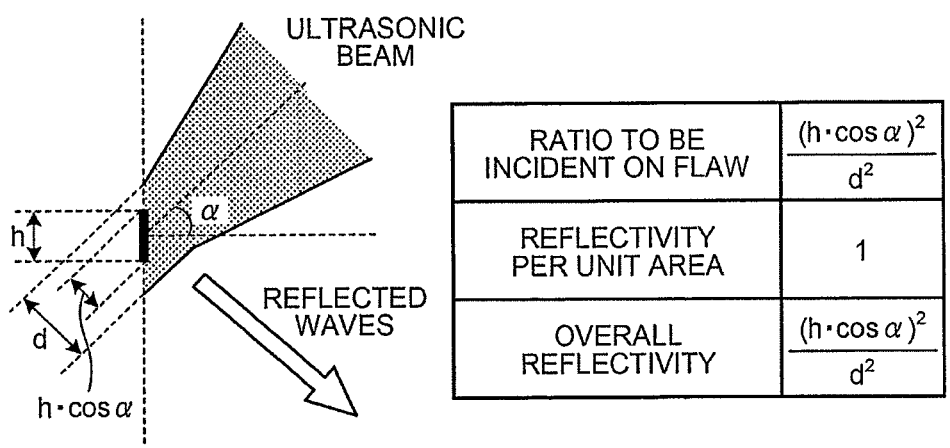
FIG. 8 is a schematic diagram for explaining reflected waves at a disc-shaped flaw.
Figure 9:
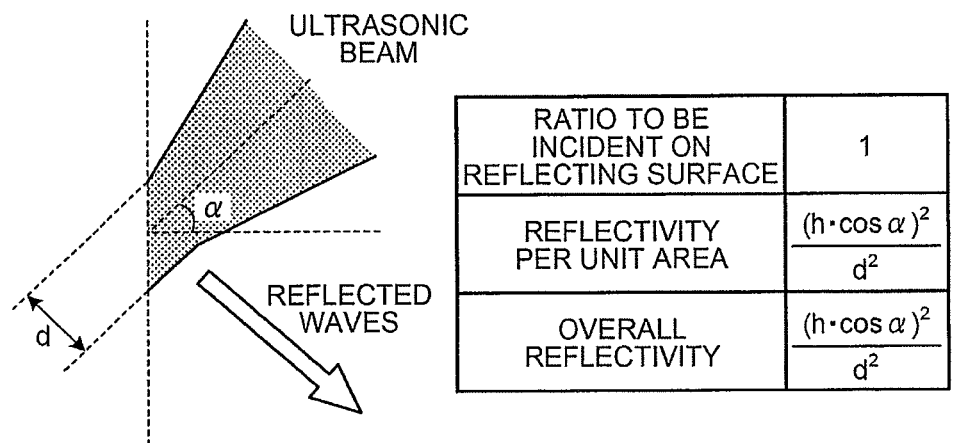
FIG. 9 is a schematic diagram for explaining reflectivity per unit area when detecting an overall reflectivity that is equivalent to that of the reflected waves at the disc-shaped flaw.

Now, with reference to FIGS. 8 and 9, described is an actual reflecting surface at which reflected waves are detectable with the overall reflectivity that is equivalent to that of the reflected waves at a flaw. FIG. 8 is a schematic diagram for explaining the reflected waves at a disc-shaped flaw of a diameter h, and FIG. 9 is a schematic diagram for explaining the reflectivity per unit area at the actual reflecting surface in detecting the reflected waves with the overall reflectivity that is equivalent to that of the reflected waves at the disc-shaped flaw of the diameter h. As illustrated in FIG. 8, when an ultrasonic beam is incident at an incident angle α onto the disc-shaped flaw of the diameter h, assuming that the reflectivity per unit area at the flaw is 1 (=100%), the ratio of the ultrasonic beam that is incident on the flaw is $(h \cdot \cos \alpha)^2/d^2$, and thus the overall reflectivity is $(h \cdot \cos \alpha)^2/d^2$. Consequently, as illustrated in FIG. 9, when detecting reflected waves of the overall reflectivity $(h \cdot \cos \alpha)^2/d^2$ equivalent to that of the reflected waves by this flaw, the ratio of the ultrasonic beam that is incident on the actual reflecting surface is 1 (=100%), and thus the reflectivity per unit area at the actual reflecting surface is $(h \cdot \cos \alpha)^2/d^2$.

Figure 10:
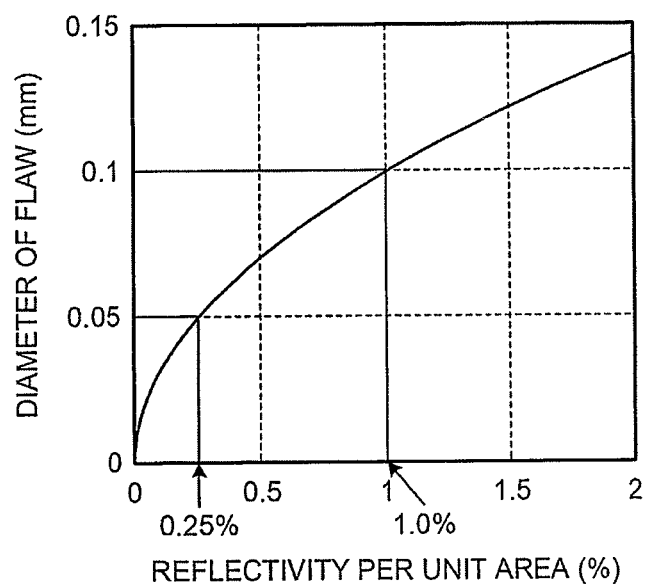
FIG. 10 is a chart illustrating the relation between the disc-shaped flaw and the reflectivity per unit area of reflected waves of the overall reflectivity that is equivalent to that of the reflected waves by the flaw.

When $\alpha=45°$ and $d=0.7$ mm are assumed, the reflectivity per unit area expressed by the foregoing expression is a function of h. FIG. 10 is a chart illustrating the relation between the disc-shaped flaw of the diameter h and the reflectivity per unit area at the actual reflecting surface at which the overall reflectivity that is equivalent to that of the reflected waves by the flaw is detected. The ordinate axis of the chart represents h and the abscissa axis represents the reflectivity per unit area. Because a flaw is detectable when $h \geq 0.05$ mm, as illustrated in FIG. 10, the reflectivity per unit area is preferably 0.25% or higher. Furthermore, because $h \geq 0.1$ mm is more preferable for the detection of flaw, as illustrated in FIG. 10, it is more preferable that the reflectivity per unit area be 1.0% or higher.

Next, described is the degree of acoustic anisotropy of a base metal portion to achieve the above-described reflectivity per unit area. In the base metal portion of carbon steel, the sound velocity in the mode (determined by the propagation direction and the displacement direction) in which the sound velocity is maximized is defined as $V_{max}$, and the sound velocity in the mode in which the sound velocity is minimized is defined as $V_{min}$. Furthermore, the sound velocity of the weld portion is isotropic regardless of the direction of propagation and is defined as $(V_{max}+V_{min})/2$. The density of the base metal portion and that of the weld portion are defined to be equal. In that case, the reflectivity per unit area R when ultrasonic waves are incident on the boundary with the weld portion in the propagation direction in which the sound velocity of the base metal portion is minimized can be expressed by the following Expression 8 (see Expression 1 in Non-Patent Literature 1).

$$R = \frac{V_{max} - V_{min}}{V_{max} + 3V_{min}} \quad (8)$$

Thus, it is preferable that the base metal portion have the acoustic anisotropy that holds the following Expression 9 true.

$$2.5 \times 10^{-3} \leq \frac{V_{max} - V_{min}}{V_{max} + 3V_{min}} \quad (9)$$

Furthermore, it is more preferable that the base metal portion have the acoustic anisotropy that holds the following Expression 10 true.

$$1.0 \times 1.0^{-2} \leq \frac{V_{max} - V_{min}}{V_{max} + 3V_{min}} \quad (10)$$

Setting of Focused Beam

In the setting of an ultrasonic beam at Step S2 in the first embodiment, even in tandem measurement, focusing the ultrasonic beam into a focused beam in the following manner can expand the tolerable range of a deviation angle $\theta$ between the virtual reflecting surface and the actual reflecting surface, that is, weaken the directivity of reflection.

Figure 11:
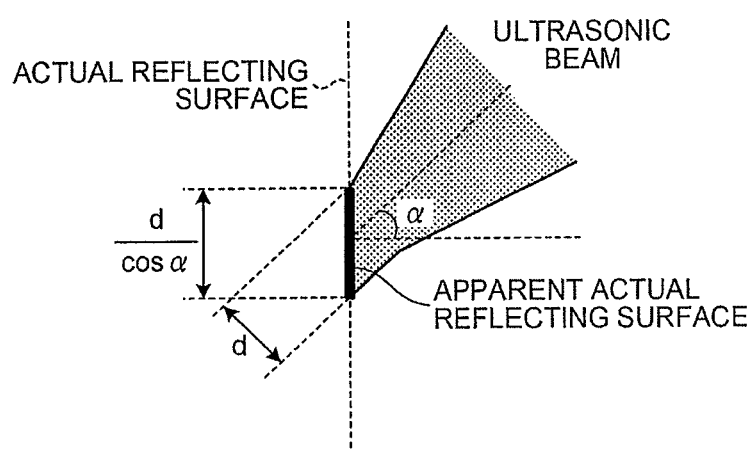
FIG. 11 is a conceptual diagram for explaining an apparent actual reflecting surface by an ultrasonic beam.

FIG. 11 is a conceptual diagram for explaining an apparent actual reflecting surface by an ultrasonic beam. As illustrated in FIG. 11, when an ultrasonic beam is incident on the actual reflecting surface, a portion that contributes to the reflection (apparent actual reflecting surface) is limited out of the actual reflecting surface. Consequently, the apparent actual reflecting surface can be regarded as a belt-like reflector of a width $2a$. At this time, by defining an incident angle $\alpha$ and a reflection angle $\beta$, because it is $a=d/2\cos \alpha$, the overall reflectivity $r'(\alpha,\beta)$ can be expressed by the following Expression 11 by using the number of waves k (see Expression 2 in Non-Patent Literature 1).

$$r'(\alpha, \beta) = \frac{\sin\left(\frac{kd}{2\cos\alpha}(\sin\beta - \sin\alpha)\right)}{\frac{kd}{2\cos\alpha}(\sin\beta - \sin\alpha)} \quad (11)$$

When the deviation angle $\theta$ between the virtual reflecting surface (incident angle $\alpha$, reflection angle $\alpha$) and the actual reflecting surface is defined, the overall reflectivity $r'(\alpha+\theta, \alpha-\theta)$ at the time the ultrasonic beam is incident can be expressed by the following Expression 12. Note that, at the time of deriving Expression 12, the addition theorem of trigonometric functions represented by Expression 13 was adapted.

$$r'(\alpha + \theta, \alpha - \theta) = \frac{\sin(kd\sin\theta)}{kd\sin\theta} = \mathrm{sinc}(kd\sin\theta) \quad (12)$$

$$\sin(\alpha + \theta) - \sin(\alpha - \theta) = 2\cos\alpha\sin\theta \quad (13)$$

Figure 12:
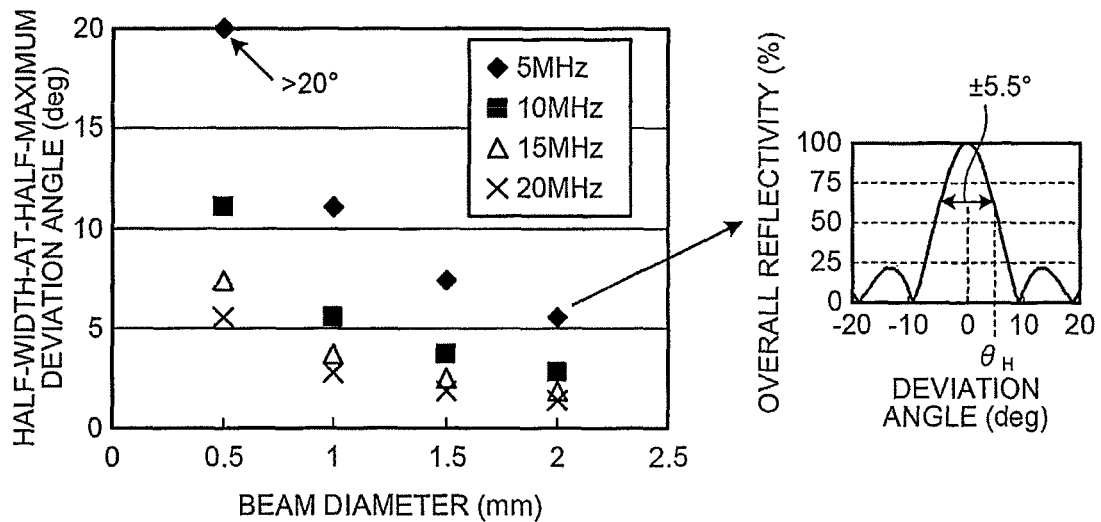
FIG. 12 is a diagram illustrating the relation among the frequency, beam diameter, and half-width-at-half-maximum deviation angle of overall reflectivity.

FIG. 12 is a diagram illustrating the relation among the frequency f, a beam diameter d, and the overall reflectivity $r'(\alpha+\theta, \alpha-\theta)$ calculated by Expression 12. In FIG. 12, with V=3200 m/s, the abscissa axis represents the beam diameter d and the ordinate axis represents the positive deviation angle $\theta_H$ (half-width-at-half-maximum deviation angle) when the overall reflectivity $r'(\alpha+\theta, \alpha-\theta)$ is 50%.

Now, because it is $\sin c(1.9) \cong 1/2$, for the positive deviation angle $\theta_H$ when the overall reflectivity $r'(\alpha+\theta, \alpha-\theta)$ is 50%, the following Expression 14 holds true.

$$kd \sin \theta_H = 1.9 \quad (14)$$

Consequently, the $\theta_H$ can be expressed by the following Expression 15.

$$\theta_H = \sin^{-1}\left(\frac{1.9}{kd}\right) \quad (15)$$

Furthermore, by expressing the number of waves k with the sound velocity $V_R$ and the frequency f of ultrasonic waves, the $\theta_H$ can be expressed by the following Expression 16.

$$\theta_H = \sin^{-1}\left(0.30 \cdot \frac{V_R}{fd}\right) \quad (16)$$

Figure 13:
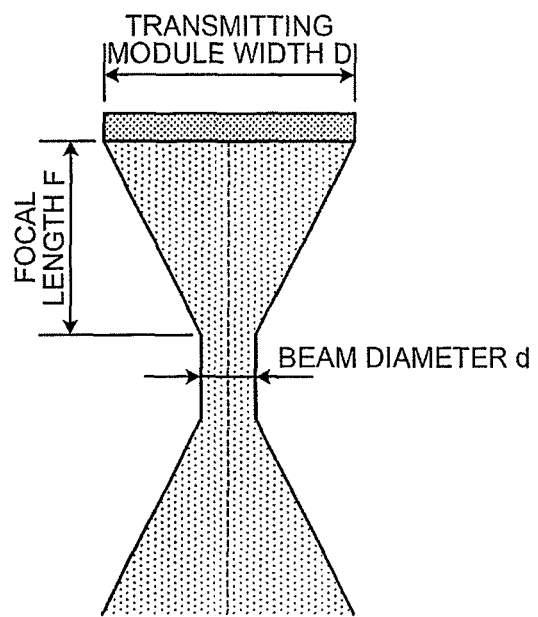
FIG. 13 is a conceptual diagram for explaining the setting of a focused beam.

FIG. 13 is a conceptual diagram for explaining the setting of a focused beam. As illustrated in FIG. 13, the focused beam is set by the beam diameter d, the transmitting unit width D, and a focal length F. Here, by using the transmitting unit width D, the focal length (coupling medium conversion)

F, the sound velocity $V_T$ of transmission waves (coupling medium), and the frequency f, the beam diameter d can be expressed as the following Expression 17 (see Non-Patent Literature 1).

$$d = \frac{FV_T}{Df} \quad (17)$$

By substituting Expression 17 into Expression 16, the $\theta_H$ can be expressed by the following Expression 18.

$$\theta_H = \sin^{-1}\left(0.30 \cdot \frac{V_R}{V_T} \cdot \frac{D}{F}\right) \quad (18)$$

Figure 14:
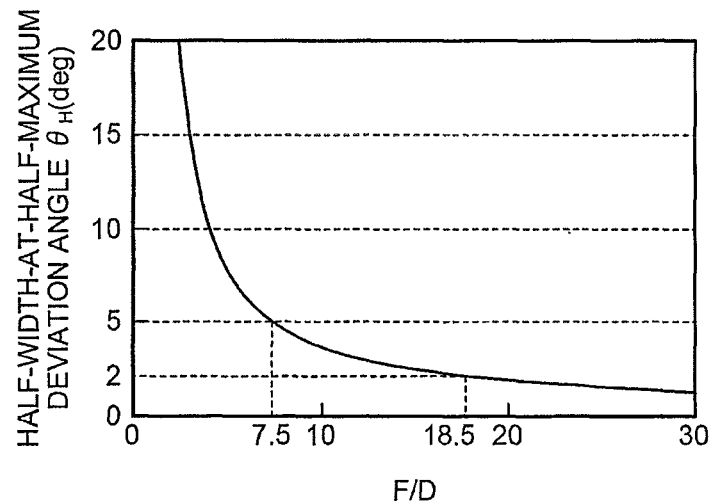
FIG. 14 is a chart illustrating the relation between the half-width-at-half-maximum deviation angle and F/D.

FIG. 14 is a chart illustrating the relation between $\theta_H$ and F/D when the sound velocity of shear waves of the test subject $V_R$=3200 m/s and the sound velocity of the coupling medium $V_T$=1480 m/s (when water is used as the coupling medium) are defined. For the half-width-at-half-maximum deviation angle $\theta_H$ to be at least $\theta_{Hlim}$ or greater here, the following Expression 19 needs to hold true with respect to the focused beam.

$$\frac{V_T}{V_R} \cdot \frac{F}{D} \leq \left(\frac{0.30}{\sin\theta_{Hlim}}\right) \quad (19)$$

It is preferable that $\theta_{Hlim}$=2° be defined. In that case, as the setting requirements for the focused beam, the following Expression 20 holds true.

$$\frac{V_T}{V_R} \cdot \frac{F}{D} \leq 8.5 \quad (20)$$

It is more preferable that $\theta_{Hlim}$=5° be defined. In that case, as the setting requirements for the focused beam, the following Expression 21 holds true.

$$\frac{V_T}{V_R} \cdot \frac{F}{D} \leq 3.4 \quad (21)$$

Figure 15:
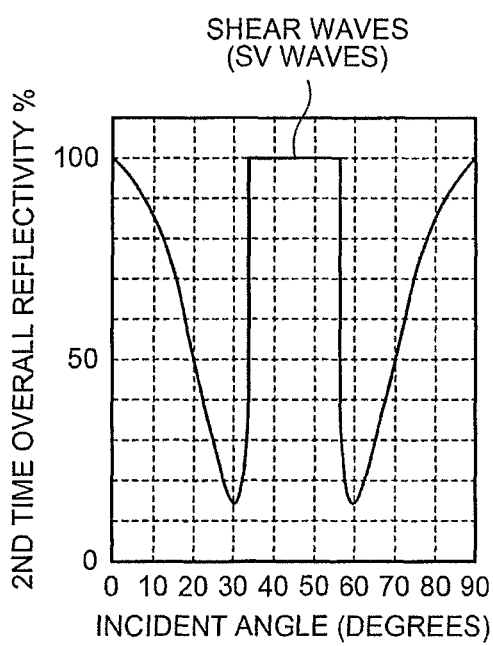
FIG. 15 is a chart for explaining a loss attributable to mode conversion from shear waves to longitudinal waves in the reflection at the boundary between a base metal portion and a weld portion and in the reflection at the inner surface of the base metal portion.

FIG. 15 is a chart for explaining a loss attributable to mode conversion from shear waves to longitudinal waves in the reflection at the boundary between the base metal portion and the weld portion and in the reflection at the inner surface of the base metal portion. The abscissa axis in the chart represents the incident angle α to the boundary with the weld portion and the ordinate axis represents the overall reflectivity of the shear waves in the reflection for the second time (reflection at the inner surface of the base metal portion) (see Patent Literature 3). When the interface between the base metal portion and the weld portion is substantially parallel to the sheet thickness direction of the base metal portion, to suppress the loss attributable to the mode conversion in the refraction at the boundary between the test subject and the coupling medium, as illustrated in FIG. 15, the incident angle α needs to be 0°≤α≤10° or 35°≤α≤55°. It is more preferable that the incident angle α be defined as 40°≤α≤50°.

As in the foregoing, in accordance with the first embodiment, because the ultrasonic waves that are incident on the boundary between the base metal portion and the weld portion of steel material are focused, the effective area of actual reflecting surface is narrowed and the reflection directivity is weakened, and thus the ultrasonic waves reflected at the boundary between the base metal portion and the weld portion of steel material can be detected easily.

First Example

Next, described is a first example that corresponds to the first embodiment in the foregoing. FIG. 16 is a diagram illustrating the setting conditions in the first example. As illustrated in FIG. 16, in the first example, for simplicity, the test subject was defined to be two dimensional. Furthermore, the base metal portion and the weld portion were defined to be different in impedance so as to emphasize the reflected waves. The frequency f of the ultrasonic array probe was set to 5 MHz. The virtual reflecting surface was defined to be in the vertical direction and the deviation angle θ with the actual reflecting surface was set to 5°. At this time, the measurement was made by defining the transmitting unit width D as 19.9 mm (20 ch), and the left-hand side ($V_T$/$V_R$)·(F/D) in the foregoing Expression 19 to Expression 21 as 2.2. Furthermore, as a comparative example by conventional technology, the measurement was made by defining the transmitting unit width D as 5.9 mm (6 ch), and the left-hand side ($V_T$/$V_R$)·(F/D) in the Expression 19 to Expression 21 as ∞ (unfocused beam).

Figure 17:
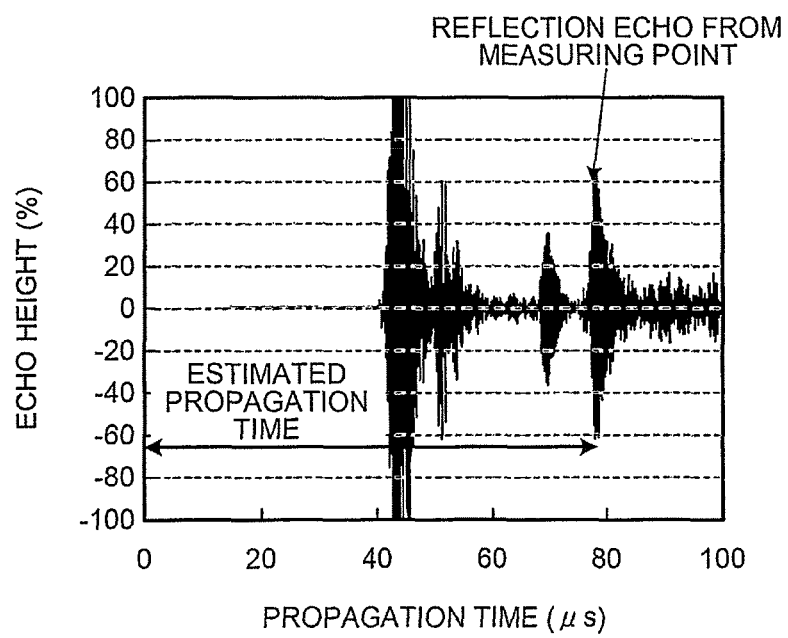
FIG. 17 is a chart illustrating the waveform of a measurement signal acquired in the first example.
Figure 18:
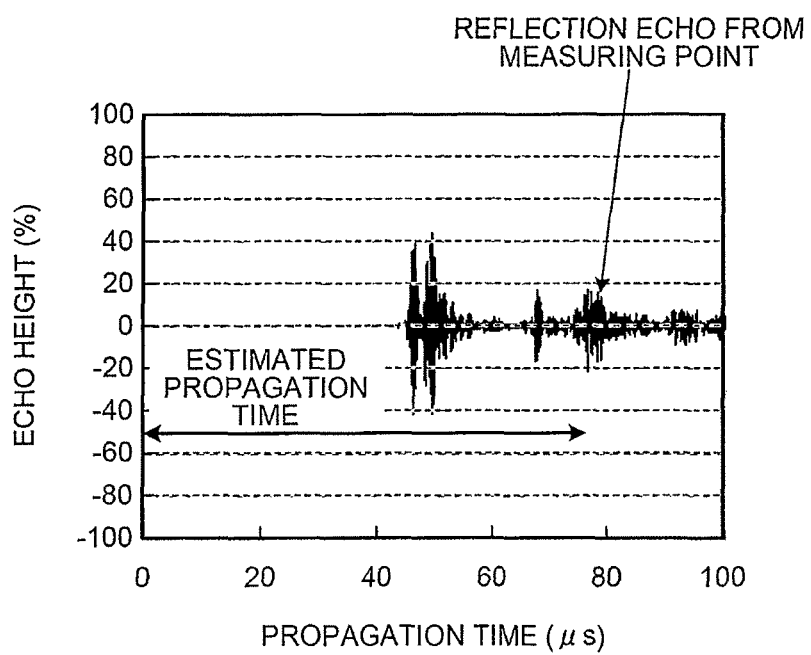
FIG. 18 is a chart illustrating the waveform of a measurement signal acquired by the conventional technology.

FIG. 17 illustrates the waveform of a measurement signal acquired in the first example, and FIG. 18 illustrates the waveform of a measurement signal acquired by the conventional technology. As illustrated in FIG. 17, although the deviation angle between the virtual reflecting surface and the actual reflecting surface is 5°, the reflected waves can be detected at a high signal level. Furthermore, as illustrated in FIG. 18, according to the conventional technology, the signal level of reflected waves is low as compared with that in the first example, and that is highly likely to cause erroneous detection.

While the first example does not refer to the weld line direction, it is only necessary to select the ultrasonic array probe by considering the beam profile in the weld line direction, and to set, according to the test subject, the width of vibrators in the weld line direction, whether the beam is a focused beam, and the focal length of the focused beam.

Second Embodiment

An ultrasonic measurement apparatus in a second embodiment takes the same configuration as that of the ultrasonic measurement apparatus 10 illustrated in FIG. 1. Furthermore, the ultrasonic measurement processing in the second embodiment defines the carbon steel the same as that in the first embodiment as the test subject. Consequently, as the requirements for the acoustic anisotropy of the base metal portion of the steel material, the above-described Expression 8 is satisfied. Furthermore, it is preferable that the base metal portion have the acoustic anisotropy that holds the foregoing Expression 9 or Expression 10 true. Meanwhile, the ultrasonic measurement processing in the second embodiment is different from the foregoing ultrasonic measurement processing in the first embodiment only in that, in the process at Step S2 illustrated in FIG. 2, instead of focusing the ultrasonic beam into a focused beam, a plurality of virtual reflecting surfaces P are assumed with a measuring point near the weld portion inside the base metal portion of the test subject as a target.

Figure 19:
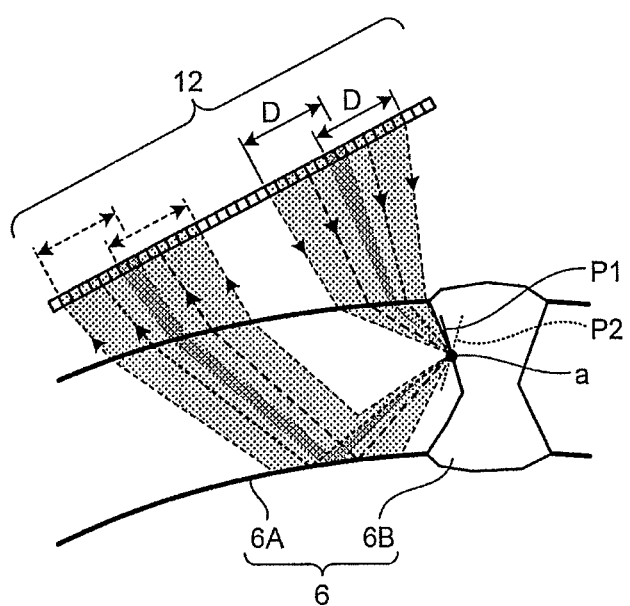
FIG. 19 is a schematic diagram illustrating a measuring point of steel material as a target of the ultrasonic array probe.

FIG. 19 is a schematic diagram illustrating a measuring point of steel material as a target of the ultrasonic array probe 12 in the second embodiment. As illustrated in FIG. 19, in the second embodiment, in the process at Step S2, the array-control calculating unit 52 assumes a plurality of virtual reflecting surfaces P with the measuring point a near the weld portion 6B inside the base metal portion 6A of the test subject 6 as a target, selects the center of a group of transmitting devices and the center of a group of receiving devices for each of the virtual reflecting surfaces (P1, P2), and sets the ultrasonic beam by calculating the propagation path. At that time, the array-control calculating unit 52 selects the transmitting unit width D of each group of transmitting devices in consideration of the beam diameter, directivity, and others.

Figure 20:
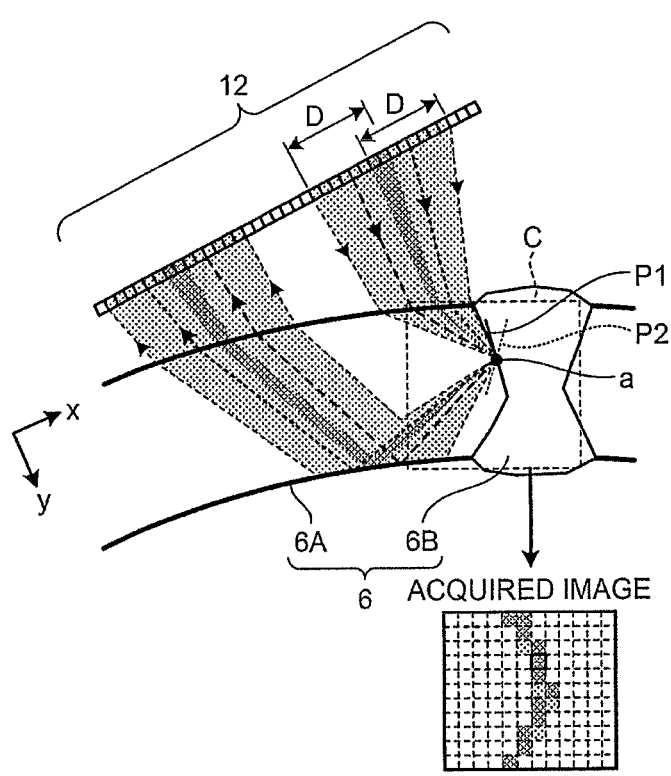
FIG. 20 is a diagram for explaining the output of measurement results to the display unit.

In this case, in the process at Step S3, the echo-height extracting unit 53 sets the detection gate, as illustrated in FIG. 6, based on each of the propagation time calculated by the array-control calculating unit 52 for the respective virtual reflecting surfaces (P1, P2), and extracts the echo height of the reflected waves received during that period. Furthermore, in the process at Step S4, as illustrated in FIG. 20, for each of the measuring points a in the evaluation target area C, the controller 5 displays an image by setting the luminance corresponding to a representative value of echo height of the measurement results acquired from the respective virtual reflecting surfaces (P1, P2) at the pixel position identified by the position of the ultrasonic array probe 12 separately detected and the position of the measuring point a determined by the measuring-point setting unit 51.

The representative value of echo height acquired from the respective virtual reflecting surfaces only needs to be defined as an average value or a maximum value of the height of the respective echoes, for example. Alternatively, the method of selecting the representative value may be changed by the measuring point. For example, it may be configured such that the echo height acquired from the virtual reflecting surface most facing the outer circumferential surface is taken when the measuring point is closer to the inner circumferential surface of the tubular test subject 6, and the echo height acquired from the virtual reflecting surface most facing the inner circumferential surface is taken when the measuring point is closer to the outer circumferential surface of the tubular test subject 6.

Setting of Plurality of Virtual Reflecting Surfaces

In the second embodiment, as in the foregoing, in the process at Step S2, even in tandem measurement, setting a plurality of virtual reflecting surfaces in the following manner can expand the tolerable range of the deviation angle $\theta$ between the virtual reflecting surface and the actual reflecting surface, that is, weaken the directivity of reflection.

As in the foregoing, when a plurality of virtual reflecting surfaces of different angles are assumed and an ultrasonic beam is incident thereon, near the virtual reflecting surface, as illustrated in FIG. 11, the portion that contributes to the reflection (apparent actual reflecting surface) is limited out of the actual reflecting surface. Consequently, the apparent actual reflecting surface can be regarded as a belt-like reflector of a width $2a$. At this time, when the incident angle $\alpha$ and the reflection angle $\beta$ are defined, because it is $a=d/2\cos\alpha$, the overall reflectivity $r'(\alpha,\beta)$ can be expressed by the following Expression 22 by using the number of waves k as the same as Expression 11 (see Expression 2 in Non-Patent Literature 1).

$$r'(\alpha, \beta) = \frac{\sin\left(\frac{kd}{2\cos\alpha}(\sin\beta - \sin\alpha)\right)}{\frac{kd}{2\cos\alpha}(\sin\beta - \sin\alpha)} \quad (22)$$

When the deviation angle $\theta$ between the virtual reflecting surface (incident angle $\alpha$, reflection angle $\alpha$) and the actual reflecting surface is defined, the overall reflectivity $r'(\alpha+\theta, \alpha-\theta)$ when the ultrasonic beam is incident can be expressed by the following Expression 23. Note that, at the time of deriving Expression 23, the addition theorem of trigonometric functions represented by Expression 24 was adapted.

$$r'(\alpha + \theta, \alpha - \theta) = \frac{\sin\left(\frac{kd}{2}\sin\theta\right)}{\frac{kd}{2}\sin\theta} \quad (23)$$

$$\sin(\alpha + \theta) - \sin(\alpha - \theta) = 2\cos\alpha\sin\theta \quad (24)$$

Figure 21:
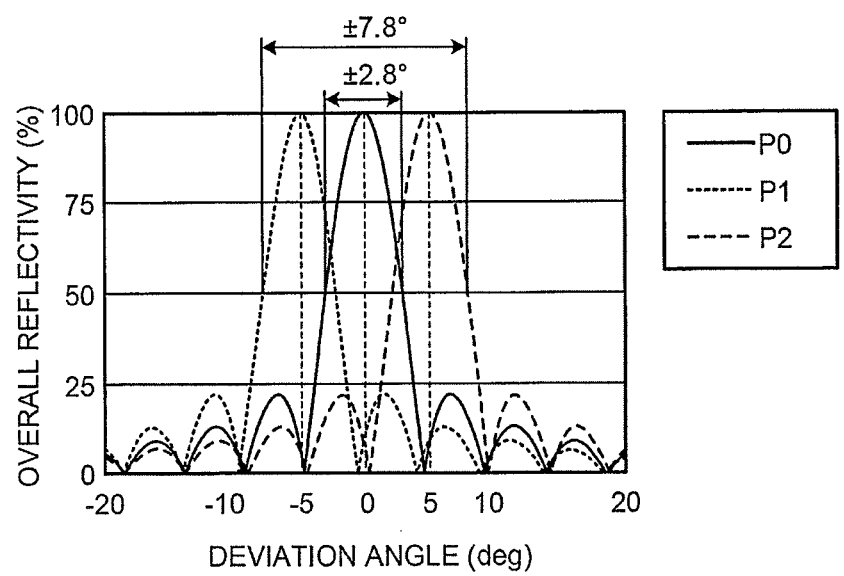
FIG. 21 is a chart illustrating the relation between the overall reflectivity at three virtual reflecting surfaces and deviation angle.

From Expression 23, it can tell that the overall reflectivity at each virtual reflecting surface is expressed as a function of deviation angle $\theta$ with respect to the actual reflecting surface. FIG. 21 is a chart illustrating the relation between the overall reflectivity of each virtual reflecting surface based on Expression 23 and the deviation angle between each virtual reflecting surface and the actual reflecting surface. As the virtual reflecting surfaces, three virtual reflecting surfaces were assumed here at 5° intervals (a virtual reflecting surface P0 of deviation angle $\theta$, a virtual reflecting surface P1 of deviation angle $\theta-5°$, and a virtual reflecting surface P2 of deviation angle $\theta+5°$. Furthermore, defined were $\alpha=45°$, beam diameter $d=2$ mm, frequency $f=10$ MHz, and $V=3200$ m/s.

As illustrated in FIG. 21, the positive deviation angle (half-width-at-half-maximum deviation angle) is 2.8° when the overall reflectivity at the virtual reflecting surface P0 of deviation angle $\theta$ is 50%. In other words, when the deviation angle $\theta$ is within 2.8°, the overall reflectivity is 50% or higher, and thus the reflected waves are detectable. Meanwhile, in the second embodiment, other than the above-described virtual reflecting surface P0, the overall reflectivity at the virtual reflecting surface P1 of deviation angle $\theta-5°$ and that at the virtual reflecting surface P2 of deviation angle $\theta+5°$ are further detected. Thus, by the half-width-at-half-maximum deviation angle of 2.8° by ($\theta-5°$) of the virtual reflecting surface P1 and the half-width-at-half-maximum deviation angle 2.8° by ($\theta+5°$) of the virtual reflecting surface P2, the range of deviation angle $\theta$ at which the overall reflectivity is 50% or higher is expanded to 7.8°. That is, it can tell that the tolerable range of deviation angle $\theta$ at which the reflected waves are detectable can be expanded by defining three virtual reflecting surfaces at 5° intervals.

When the above discussion is described more generally, for a positive value $2\theta_{1/2}$ (take a minimum value if many) that satisfies the following Expression 25 for which the right-hand side of Expression 23 is defined as 0.5, it only needs to set a plurality of virtual reflecting surfaces such that the angular difference for each virtual reflecting surface is $2\theta_{1/2}$ or smaller.

$$0.5 = \frac{\sin\left(\frac{kd}{2}\sin\theta_{1/2}\right)}{\frac{kd}{2}\sin\theta_{1/2}} \quad (25)$$

As in the foregoing, when the interface between the base metal portion and the weld portion is substantially parallel to the sheet thickness direction of the base metal portion, to reduce the loss due to the mode conversion in the reflection at the inner surface of the base metal portion and in the refraction at the boundary between the test subject and the coupling medium, as illustrated in FIG. 15, the incident angle α needs to be 0°≤α≤10° or 35≤α≤55°. More preferably, the incident angle α is defined as 40°≤α≤50°.

As in the foregoing, in accordance with the second embodiment, because the reflected waves are measured by setting a plurality of virtual reflecting surfaces for the ultrasonic waves that are incident on the boundary between the base metal portion and the weld portion of steel material, the directivity of reflection of the reflected waves are weakened, and thus the ultrasonic waves reflected at the boundary between the base metal portion and the weld portion of steel material can be detected easily.

Furthermore, by implementing the first embodiment and the second embodiment at the same time, the reflected waves may be measured by focusing the ultrasonic waves that are incident on the boundary between the base metal portion and the weld portion of steel material and setting a plurality of virtual reflecting surfaces.

Second Example

Next, described is a second example that corresponds to the above-described second embodiment. FIG. 22 is a diagram illustrating the setting conditions in the second example. As illustrated in FIG. 22, in the second example, for simplicity, the test subject was defined to be two dimensional. Furthermore, the base metal portion and the weld portion were defined to be different in impedance so as to emphasize the reflected waves. The frequency f of the ultrasonic array probe was set to 5 MHz. The actual reflecting surface is assumed to be inclined by 5° from the vertical direction, and the measurement was made by setting two virtual reflecting surfaces of 0° and 5° inclinations from the vertical direction as the virtual reflecting surfaces and by a non-focused beam being incident.

Figure 23:
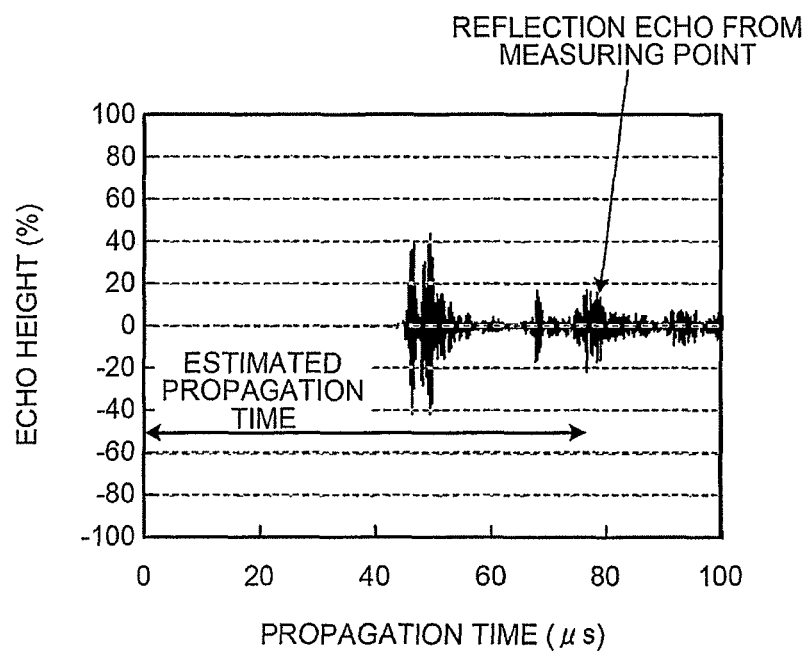
FIG. 23 is a chart illustrating the waveform of a measurement signal acquired by the conventional technology.
Figure 24:
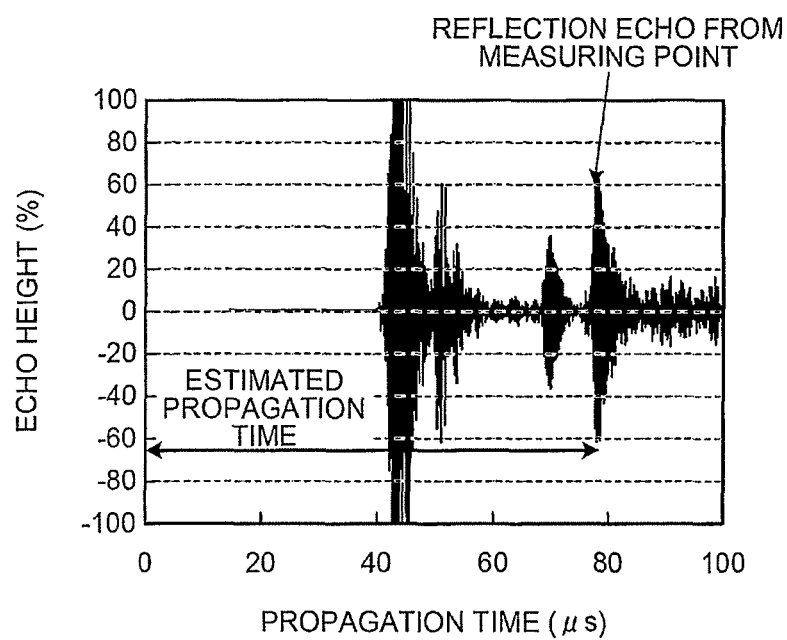
FIG. 24 is a chart illustrating the waveform of a measurement signal acquired in the second example.
Figure 25:
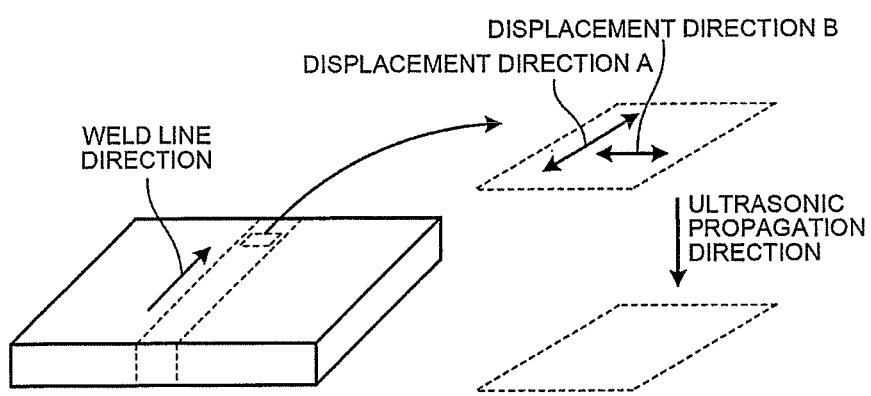
FIG. 25 is a diagram illustrating shear wave velocity measured at a weld portion of carbon steel welded by conventional submerged arc welding, and reflectivity calculated based on the shear wave velocity measured.
Figure 26:
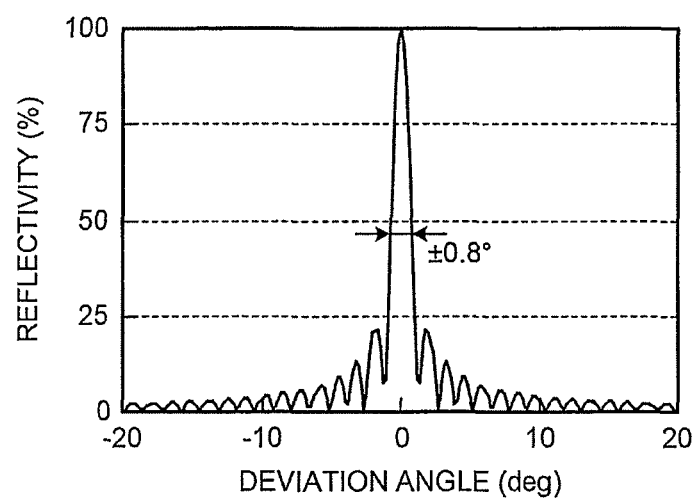
FIG. 26 is a chart illustrating the relation between the deviation angle between a virtual reflecting surface and an actual reflecting surface and the reflectivity.

FIG. 23 illustrates the waveform of a measurement signal acquired when the inclination of the virtual reflecting surface from the vertical direction is 0° (deviation angle to actual reflecting surface is)5°, and FIG. 24 illustrates the waveform of a measurement signal acquired when the inclination of the virtual reflecting surface from the vertical direction is 5° (deviation angle to actual reflecting surface is 0°). According to the conventional technology, as illustrated in FIG. 23, when the virtual reflecting surface has the deviation angle of 5° to the actual reflecting surface, the signal level of reflected waves is low, and it is difficult to detect. Meanwhile, according to the second example, by setting a plurality of virtual reflecting surfaces, the optimal measurement is made at any one of the virtual reflecting surfaces with respect to the actual reflecting surface at all times and the measurement signal indicated in FIG. 23 and the measurement signal indicated in FIG. 24 are detected, and thus the reflected waves can be detected at a high signal level.

While the second example does not refer to the weld line direction, it is only necessary to select the ultrasonic array probe by considering the beam profile in the weld line direction, and to set, according to the test subject, the width of vibrators in the weld line direction, whether the beam is a the focused beam, and the focal length of the focused beam.

INDUSTRIAL APPLICABILITY

As in the foregoing, the ultrasonic measurement method and the ultrasonic measurement apparatus according to the present invention are suitable for evaluating the quality of a weld portion of steel material in a non-destructive manner by using ultrasonic waves.

REFERENCE SIGNS LIST 1 measurement-signal acquiring unit
11 transmitting unit
12 ultrasonic array probe
13 receiving unit
2 input unit
3 storage unit
4 display unit
5 controller
10 ultrasonic measurement apparatus

The invention claimed is:

1. An ultrasonic measurement method comprising:
a measuring point setting step of setting an arbitrary measuring point near a weld portion inside of steel material and assuming a virtual reflecting surface that includes the measuring point and is parallel to a weld line direction;
a focused beam setting step of transmitting ultrasonic waves of a shear wave mode satisfying Expression 1 and focusing onto the measuring point via a coupling medium at a predetermined incident angle with respect to the virtual reflecting surface;
a detecting step of detecting reflected waves of the transmitted ultrasonic waves at a boundary between a base metal portion and the weld portion; and
an evaluating step of evaluating a shape of the weld portion based on the reflected waves:

$$\frac{V_T}{V_R} \cdot \frac{F}{D} \leq \frac{0.30}{\sin\theta_{Hlim}} \quad (1)$$

where $V_T$ (mm/s) is sound velocity of the coupling medium,
$V_R$ (mm/s) is sound velocity of shear waves at the base metal portion of the steel material as a test subject,
D (mm) is a transmitting unit width in a direction orthogonal to the weld line direction,
F (mm) is a focal length in coupling medium conversion, and
$\theta_{Hlim}$ (degrees) is a deviation angle upper limit between the assumed reflecting surface and an actual reflecting surface.

2. The ultrasonic measurement method according to claim 1, wherein a plurality of virtual reflecting surfaces of different angles are assumed for each measuring point set at the measuring point setting step.

3. The ultrasonic measurement method according to claim 2, wherein the virtual reflecting surfaces for which areas in a normal direction are continuous are assumed such that transmission and reception efficiency of at least one of the virtual reflecting surfaces is 0.5 or higher while the transmission and reception efficiency is 1 when the virtual reflecting surface coincides with an actual reflecting surface.

4. The ultrasonic measurement method according to claim 2, wherein the deviation angle upper limit $\theta_{Hlim}$ is 2°.

5. The ultrasonic measurement method according to claim 2, wherein the base metal portion of the steel material satisfies Expression 2 with respect to sound velocity $V_{max}$ in a mode in which the sound velocity is maximized and sound velocity $V_{min}$ in a mode in which the sound velocity is minimized:

$$2.5 \times 10^{-3} \leq \frac{V_{max} - V_{min}}{V_{max} + 3V_{min}}. \tag{2}$$

6. The ultrasonic measurement method according to claim 2, wherein the incident angle is an angle formed between a transmission direction of the ultrasonic waves and a normal direction of the virtual reflecting surface at the measuring point and is 0° or greater and 10° or smaller or is 35° or greater and 55° or smaller.

7. The ultrasonic measurement method according to claim 2, wherein transmission and reception of the ultrasonic waves are performed while changing the measuring point by using an array probe for the transmission and reception of the ultrasonic waves and by switching electronic beam control of the array probe.

8. The ultrasonic measurement method according to claim 1, wherein the deviation angle upper limit $\theta_{Hlim}$ is 2°.

9. The ultrasonic measurement method according claim 1, wherein the base metal portion of the steel material satisfies Expression 2 with respect to sound velocity $V_{max}$ in a mode in which the sound velocity is maximized and sound velocity $V_{min}$ in a mode in which the sound velocity is minimized:

$$2.5 \times 10^{-3} \leq \frac{V_{max} - V_{min}}{V_{max} + 3V_{min}}. \tag{2}$$

10. The ultrasonic measurement method according to claim 1, wherein the incident angle is an angle formed between a transmission direction of the ultrasonic waves and a normal direction of the virtual reflecting surface at the measuring point and is 0° or greater and 10° or smaller or is 35° or greater and 55° or smaller.

11. The ultrasonic measurement method according to claim 1, wherein transmission and reception of the ultrasonic waves are performed while changing the measuring point by using an array probe for the transmission and reception of the ultrasonic waves and by switching electronic beam control of the array probe.

12. An ultrasonic measurement apparatus comprising:
a measuring-point setting unit that sets an arbitrary measuring point near a weld portion inside of steel material and assumes a virtual reflecting surface that includes the measuring point and is parallel to a weld line direction;
a focused-beam setting unit that transmits ultrasonic waves of a shear wave mode satisfying Expression 3 and focusing onto the measuring point via a coupling medium at a predetermined incident angle with respect to the virtual reflecting surface;
a detector that detects reflected waves of the transmitted ultrasonic waves at a boundary between a base metal portion and the weld portion; and
an evaluating unit that evaluates a shape of the weld portion based on the reflected waves:

$$\frac{V_T}{V_R} \cdot \frac{F}{D} \leq \frac{0.30}{\sin\theta_{Hlim}} \tag{3}$$

where $V_T$ (mm/s) is sound velocity of the coupling medium,
$V_R$ (mm/s) is sound velocity of shear waves at the base metal portion of the steel material as a test subject,
D (mm) is a transmitting unit width in a direction orthogonal to the weld line direction,
F (mm) is a focal length in coupling medium conversion, and
$\theta_{Hlim}$ (degrees) is a deviation angle upper limit between the assumed reflecting surface and an actual reflecting surface.

* * * * *